United States Patent [19]
Eichhorn et al.

[11] Patent Number: 6,110,207
[45] Date of Patent: Aug. 29, 2000

[54] IMPLANT FOR SECURING A TENDON REPLACEMENT MEMBER

[75] Inventors: Juergen Eichhorn, Mitterfels; Nicola Giordano, Villingen-Schwenningen; Karl-Ernst Kienzle, Immendingen, all of Germany

[73] Assignee: Aesculap AG & Co. KG, Tuttlingen, Germany

[21] Appl. No.: 09/178,005

[22] Filed: Oct. 21, 1998

Related U.S. Application Data

[63] Continuation of application No. PCT/EP97/01292, Mar. 14, 1997.

[30] Foreign Application Priority Data

Apr. 23, 1996 [DE] Germany ............................ 196 16 122

[51] Int. Cl.⁷ ..................................................... A61F 2/08
[52] U.S. Cl. ....................................... 623/13.14; 606/232
[58] Field of Search ........................... 623/13, 20, 16–19, 623/21–23, 13.14; 606/73, 232

[56] References Cited

U.S. PATENT DOCUMENTS

| | | |
|---|---|---|
| 3,206,018 | 9/1965 | Lewis et al. . |
| 3,896,500 | 7/1975 | Rambert et al. ............................ 128/92 |
| 4,744,793 | 5/1988 | Parr et al. .................................. 623/13 |
| 5,139,520 | 8/1992 | Rosenberg ................................ 623/13 |
| 5,306,301 | 4/1994 | Graf et al. . |

FOREIGN PATENT DOCUMENTS

| | | |
|---|---|---|
| 0232049 | 8/1987 | European Pat. Off. . |
| 0 317 408 | 5/1989 | European Pat. Off. . |
| 89 14 308 | 5/1990 | Germany . |
| 90 02 844 | 1/1991 | Germany . |
| 296 07 352 | 9/1996 | Germany . |
| 1600752 | 12/1988 | U.S.S.R. . |
| 92/16167 | 10/1992 | WIPO . |

*Primary Examiner*—David H. Willse
*Assistant Examiner*—Choon P. Koh
*Attorney, Agent, or Firm*—Barry R. Lipsitz; Douglas M. McAllister

[57] ABSTRACT

To be able to secure the tendon replacement member without additionally weakening the tibia in the case of an implant for securing a tendon replacement member to a channel receiving the tendon replacement member in the region of the tibia close to the knee, it is proposed that the implant is in the form of a disc with passages for threads connected to the tendon replacement member and is dimensioned so that it completely covers the outlet opening of the channel from the tibia.

8 Claims, 2 Drawing Sheets

FIG. 2
FIG. 3
FIG. 4
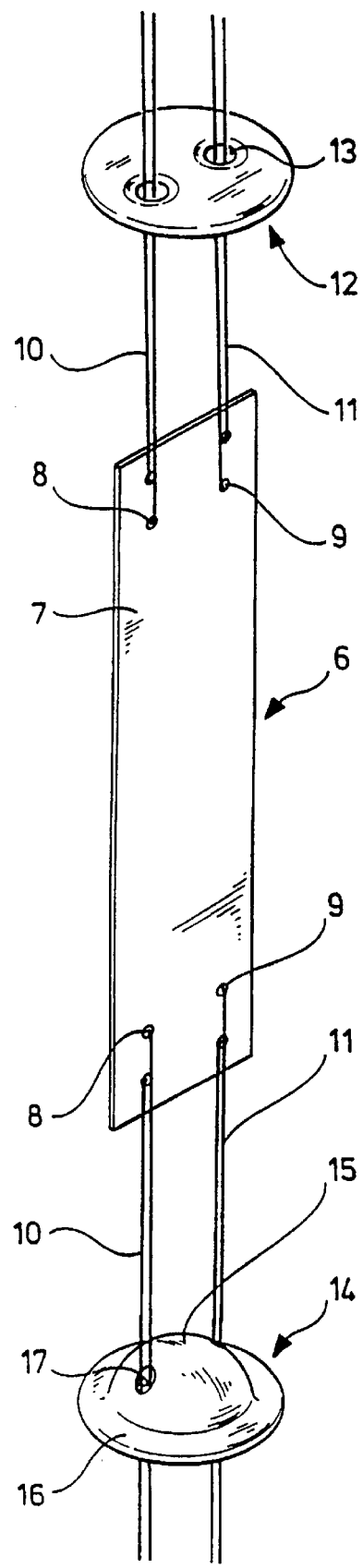
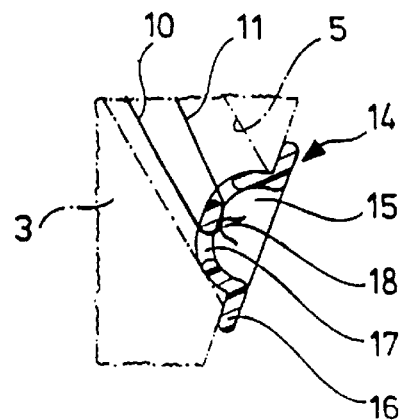
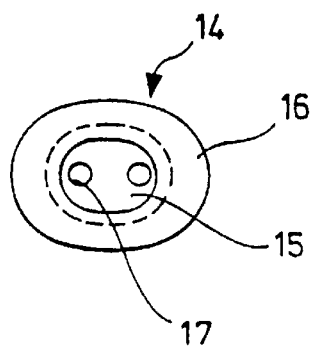

IMPLANT FOR SECURING A TENDON REPLACEMENT MEMBER

The present invention continuation of application PCT/EP 97/01292 of Mar. 14, 1997, the entire specification of which is incorporated herein by reference.

The invention relates to an implant for securing a tendon replacement member to a channel receiving the tendon replacement member in the region of the tibia close to the knee in the form of a disc with passages for threads connected to the tendon replacement member, which is dimensioned so that it completely covers the outlet opening of the channel from the tibia.

It is known to use tendon replacement members, which are inserted into cavities passing through the femur and the tibia in the region close to the knee and secured there with threads fastened to the tendon replacement member outside the femur or tibia, for replacement of destroyed cruciate ligaments in the knee joint (U.S. Pat No. 5,139,520). While the threads on the outlet of the corresponding femur channel on the femur side are secured by means of a knob-like implant, at the outlet opening of the tibia channel on the tibia side it is necessary to insert a bone screw into the tibia below this outlet opening and secure the threads to it. As a result, a further opening must be provided in the tibia next to the channel passing through this to enable the bone screw to be inserted into this further opening. This results in further weakening of the tibia.

An implant of the aforementioned type is described in DE 90 02 844 U1 which comprises a disc which is essentially plane and in the centre has a web protruding to both sides. Passages are arranged in the plane disc on both sides of the web.

Working from this prior art, it is an object of the invention to construct an implant of the aforementioned type in such a way that it is suitable for securing a tendon replacement member without the implant projecting unnecessarily outwards.

This object is achieved according to the invention with an implant of the above-described type in that it has a bulging central region, which forms a central depression on the side remote from the bone and a projection dipping into the channel on the side facing the bone, and that a plane circumferential edge strip adjoins the central region on the outside.

The configuration is particularly favourable and allows, on the one hand, the implant to be securely fixed in the drilled hole in the tibia and, on the other hand, this implant projects outwards to an extremely small degree so that the implant can remain in the body after the operation without problem. It is important here that the bulging region on one side acts as centring projection, which dips into the drill hole in the bone, while on the other side it can receive the knots of threads, so that these likewise do not project outwards. Because this central bulging region is surrounded by a plane edge strip, the disc is supported on the bone by this edge strip, i.e. in the region of the edge surrounding the drilled hole in the bone. This results in a secure centred fixture, on the one hand, and a very close abutment of the implant against the bone, on the other.

The passages are preferably arranged in the central region so that the threads terminate inside the depression formed by the central region and can be knotted there.

In a preferred embodiment, the outer edge of the disc-shaped implant can be in circular form, but it is also favourable if, in another embodiment, this outer edge is of oval construction.

In an embodiment, the bulging central region can essentially have the shape of a spherical segment, and in another preferred embodiment, the bulging central region has an oval boundary line.

It is favourable if the implant is made of titanium.

An implant with a central bulging region can be used particularly advantageously as a replacement for a known bone screw on the tibia side. However, it would also be possible in principle to arrange an implant constructed in this way on other bone channels in order to secure tendon replacement members there, e.g. also at the outlet of the femur channel in the case of a cruciate ligament replacement member.

The following description of preferred embodiments of the invention serves for more detailed explanation in association with the drawing:

FIG. 2 is a schematic view of a tendon replacement member with threads secured at its ends and with securing implants at both ends;

FIG. 3 is a view in longitudinal section of an implant of oval shape inserted into the drilled hole in the bone, and FIG. 4 is a plan view onto the oval implant of FIG. 3.

Figure 1:
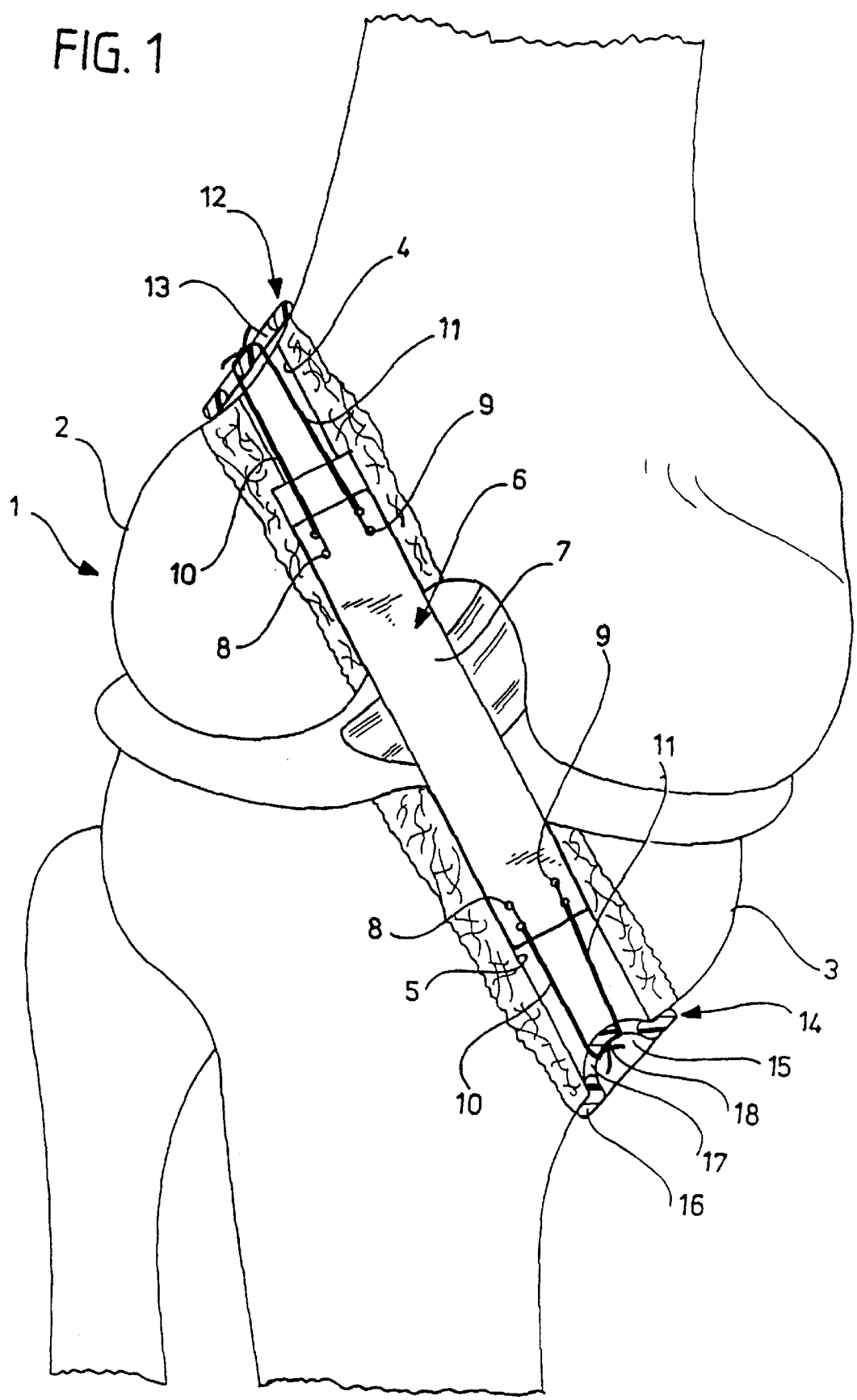
FIG. 1 is a side view in broken representation of a knee joint with a cruciate ligament replacement member in the region of the bone channels.

In order to replace a destroyed cruciate ligament in a knee joint 1 longitudinal channels 4 and 5 are respectively drilled into the femur head 2 and the tibia head 3, said channels being essentially aligned to one another when the knee joint is extended and running from the front side to the rear side of the knee joint, passing obliquely through this.

A cruciate ligament replacement member 6 is drawn into the longitudinal channels 4 and 5, said replacement member comprising a band-shaped piece 7 of a tendon replacement member, e.g. a part of the patella tendon, on the ends of which threads 10, 11 drawn through openings 8, 9 are arranged, e.g. two threads 10 and 11 arranged adjacent to one another at both ends, as is evident from the representation in FIG. 2.

To secure the piece 7 in the longitudinal channels 4, 5, the threads 10, 11 are directed outwards out of the longitudinal channels 4, 5 and secured there. At the outlet of the longitudinal channel 4 a knob-shaped implant 12 is arranged with two passages 13, through which the threads 10, 11 are passed. These are knotted together on the side of the implant 12 remote from the bone so that the threads 10, 11 are held on the implant 12 abutting against the femur head 2 (FIG. 1).

On the opposing side in the region of the outlet of the longitudinal channel 5 from the tibia head 3, an implant 14 is used which comprises a spherically bulging central region 15 and a plane edge strip 16 surrounding this in a ring shape, so that the implant 14 has a hat-shaped appearance. In the central region 15 two passages 17 are provided through which the threads 10, 11 are drawn.

The implant 14 is pushed into the outlet opening of the longitudinal channel 5 so that the inwardly bulging central region 15 dips into the longitudinal channel 5 and thus centres the hat-shaped implant 4 in the outlet opening. In this case, the edge strip 16 abuts against the outer surface of the tibia head 3 surrounding the outlet opening of the longitudinal channel 5.

The two threads 10 and 11 passing through the passages 17 are knotted together on the side remote from the longitudinal channel 5, and the resulting knot 18 is received in the trough of the central region 15 remote from the bone so that the knot 18 does not protrude outwards over the contour of the implant (FIG. 1).

The implant 14 can be produced by a bulging deformation of the central region 15, and can preferably be made of titanium and remain in the body, if required. It would also be possible, in principle, to produce the implant from an absorbable plastic material.

In the implant shown in FIGS. 1 and 2 the edge is circular in construction, the central region bulges in the shape of a spherical segment, and therefore this implant is particularly suitable when the outlet opening of the bone channel to be covered is circular.

In the embodiment according to FIGS. 3 and 4, in which corresponding parts bear the same reference numerals, a modification has been made in that the implant is of oval construction, i.e. the edge is oval, as is the central region, which has a bulge for formation of the projection and depression. This bulge merges with an oval boundary line into the plane edge strips of the cup-shaped implant so that the projection is constructed longer in one direction than in the direction running transversely thereto. As a result, this implant is particularly suitable for use in bone channels which terminate with an oval outlet opening. In this case, the projection can be inserted positively into this oval outlet opening.

What is claimed is:

1. An implant for securing a tendon replacement member to a channel receiving the tendon replacement member in the region of the tibia close to the knee in the form of a disc with two passages located in a bulging central region for threads connected to the tendon replacement member, said bulging central region being dimensioned so that it completely covers the outlet opening of the channel from the tibia, wherein:

the bulging central region forms a central depression on the side remote from the bone and a projection dipping into the channel on the side facing the bone, and a plane circumferential edge strip adjoins the central region on the outside.

2. An implant according to claim 1, wherein the disc has a circular edge.

3. An implant according to claim 1, wherein the disc has an oval edge.

4. An implant according to claim 1, wherein the bulging central region essentially has the shape of a spherical segment.

5. An implant according to claim 2, wherein the bulging central region essentially has the shape of a spherical segment.

6. An implant according to claim 1, wherein the bulging central region has an oval boundary line.

7. An implant according to claim 3, wherein the bulging central region has an oval boundary line.

8. An implant according to claim 1, wherein the implant is made of titanium.

* * * * *